(12) United States Patent
Perrin et al.

(10) Patent No.: US 7,265,106 B2
(45) Date of Patent: Sep. 4, 2007

(54) METHOD FOR ISOLATING (R)-TOFISOPAM

(75) Inventors: Scott R. Perrin, Boothwyn, PA (US); Kimm B. Galbraith, Spring City, PA (US); Naidong Ye, Malvern, PA (US)

(73) Assignee: Vela Aquisition Corporation, Ewing, NJ (US)

( * ) Notice: Subject to any disclaimer, the term of this patent is extended or adjusted under 35 U.S.C. 154(b) by 362 days.

(21) Appl. No.: 10/841,075

(22) Filed: May 7, 2004

(65) Prior Publication Data

US 2004/0254174 A1    Dec. 16, 2004

Related U.S. Application Data

(60) Provisional application No. 60/469,456, filed on May 9, 2003.

(51) Int. Cl.
C07D 243/00 (2006.01)
A61K 31/55 (2006.01)
A61P 25/00 (2006.01)

(52) U.S. Cl. .................... 514/221; 540/567
(58) Field of Classification Search ........... 514/221; 540/567

See application file for complete search history.

(56) References Cited

U.S. PATENT DOCUMENTS

| 5,202,433 | A | 4/1993 | Okamoto et al. | 540/200 |
|---|---|---|---|---|
| 6,080,736 | A | 6/2000 | Landry | 514/221 |
| 6,638,928 | B1 * | 10/2003 | Harris et al. | 514/221 |
| 6,864,251 | B2 * | 3/2005 | Kucharik et al. | 514/221 |
| 7,022,700 | B2 * | 4/2006 | Harris et al. | 514/221 |
| 2004/0152695 | A1 * | 8/2004 | Harris et al. | 514/221 |
| 2004/0157833 | A1 * | 8/2004 | Harris et al. | 514/221 |

FOREIGN PATENT DOCUMENTS

| HU | 178516 | 3/1983 |
|---|---|---|
| WO | WO 02/094189 | 11/2002 |

OTHER PUBLICATIONS

Bargmann-Leyder et al., A Comparison of LC and SFC for Cellulose- and Amylose- Derived Chiral Stationary Phases, Chirality, vol. 7, No. 5, pp. 311-325, 1995.*

M. Simonyi et al., "Stereoselective Binding of a 2,3-Benzodiazepine to Human Serum Albumin", Biochemical Pharmacology. vol. 32, No. 12, pp. 1917-1920, 1983.

J. Visy et al., "The Role of Configuration and Conformation in the Binding of 2,3-Benzodiazepines to Human Serum Albumin", CHIRALITY 1:271-275 (1989)..

M. Rizzo, "Chromatographic separation of 2,3-benzodiazepines", Journal of Chromatography B, 747 (2000) 203-216.

B. Chankvetadze et al., "Dimethyl-, dichloro- and chloromethylphenylcarbamates of amylase as chiral stationary phases for high-performance liquid chromatography", Journal of Chromatography A, 694 (1995) 101-109.

"Whelk-O 1 Chiral Stationary Phase for many Enantioseparations", VWR International Ltd, 2000, '01, '02, '03; http://www.chromatography.co.us/APPS/HPCL/WHELKAPP.HTM, downloaded Apr. 14, 2003.

Geoffrey Cox, Ph.D. et al., "New High Performance Amylose Chiral Columns: CHIRALPAK AS-H and CHIRALPAK AS-RH", The Application Notebook (Jun. 2002).

Chromatography Catalog, pp. 16-28, Regis Technologies, Inc. (2002).

* cited by examiner

*Primary Examiner*—Brenda Coleman
(74) *Attorney, Agent, or Firm*—Drinker Biddle & Reath LLP; Daniel A. Monaco

(57) ABSTRACT

(R)-tofisopam, substantially free of the (S)-enantiomer of tofisopam, is obtained by separating the enantiomers of tofisopam by chromatography employing a chiral separation medium comprising (i) (2S)-2-{(1S)[(3,5-dinitrophenyl)carbonylamino]phenylmethyl}-3,3-dimethylbutanoate, covalently bound to silica through an alkylene ester linkage or (ii) an amylose derivative of formula I:

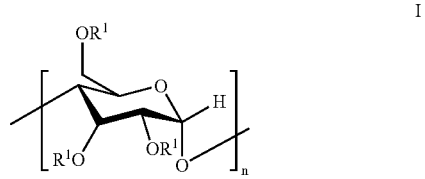

wherein each $R^1$ and n are defined herein; the amylose derivative being coated on a porous inorganic carrier or a porous organic carrier.

25 Claims, 6 Drawing Sheets

METHOD FOR ISOLATING (R)-TOFISOPAM

This application claims the benefit of U.S. Provisional Application No. 60/469,456 filed May 9, 2003.

FIELD OF THE INVENTION

The present invention relates to the preparative-scale isolation of (R)-tofisopam via chromatographic resolution of racemic tofisopam employing a chiral separation medium.

BACKGROUND OF THE INVENTION

Tofisopam-Physical Properties/Chemistry

Tofisopam (structure shown below, with the atom numbering system indicated) demonstrates potent CNS modulating activity. Tofisopam is 1-(3,4-dimethoxyphenyl)-4-methyl-5-ethyl-7,8-dimethoxy-5H-2,3-benzodiazepine.

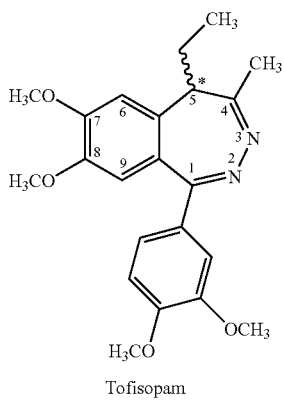

Tofisopam

Tofisopam exists as a racemic mixture of (R)- and (S)-enantiomers. This is due to the asymmetric carbon (indicated by *) at the 5-position of the benzodiazepine ring. An asymmetric carbon is a carbon atom with four different groups attached.

The molecular structure and conformational properties of tofisopam have been determined by NMR, CD and X-ray crystallography. See, Visy et al., *Chirality* 1:271-275 (1989); the entire disclosure of which is incorporated herein by reference. In addition to existing as (R)- and (S)-enantiomers, each enantiomer of tofisopam exists in two stable conformations that may be assumed by the benzodiazepine ring as generally depicted below.

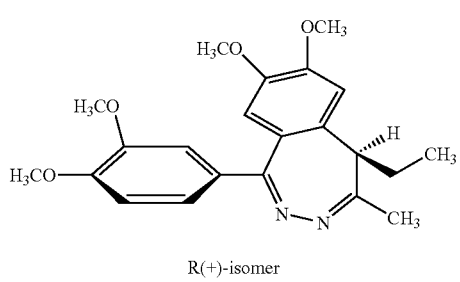

R(+)-isomer

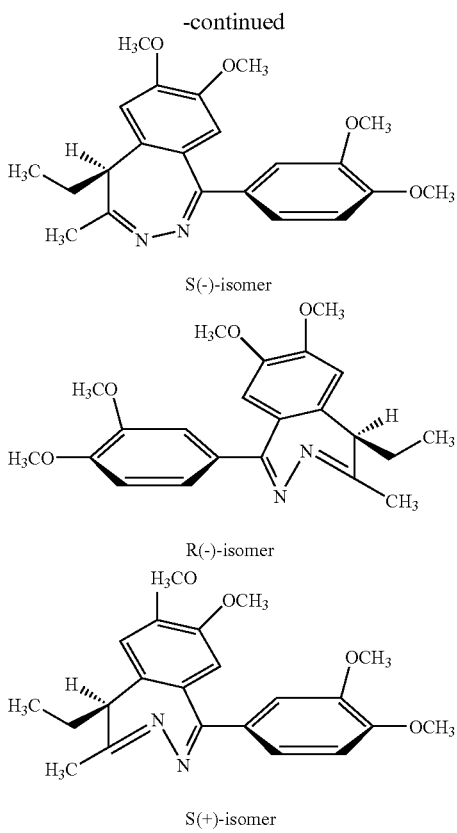

S(-)-isomer

R(-)-isomer

S(+)-isomer

The sign of the optical rotation is reversed upon inversion of the diazepine ring from one conformer to the other. The major conformers, (R)-(+) and (S)-(−) have the 5-ethyl group in a quasi-equatorial position, while in the minor conformers, (R)-(−) and (S)-(+), the 5-ethyl group is positioned quasi-axially. Thus, racemic tofisopam can exist as four molecular species, i.e., two enantiomers, each of which exists in two conformations. In crystal form, tofisopam exists only as the major conformations, with dextrorotatory tofisopam being of the (R) absolute configuration. See, Toth et al., *J. Heterocyclic Chem.*, 20:709-713 (1983); *Bioorganic Heterocycles*, Van der Plas, H. C., Ötvös, L, Simongi, M., eds. Budapest Amsterdam: Akademia; Kiado-Elsevier, 229: 233 (1984); the entire disclosures of which are incorporated herein by reference.

The (R)- and (S)-enantiomers of tofisopam have been shown to possess different biological activity profiles. In particular, the use of the (R)-enantiomer of tofisopam, substantially free of the (S)-enantiomer of tofisopam, has been shown to be useful in the treatment of anxiety, resulting in diminished adverse effects and accordingly an improved therapeutic index as compared to administration of racemic tofisopam. See, U.S. Pat. No. 6,080,736, the entire disclosure of which is incorporated herein by reference.

Tofisopam—Synthetic Preparation of the Racemate

Racemic tofisopam is prepared by reacting 3,4,3',4'-tetramethoxy-6-(α-aceto-propyl)benzophenone with hydrazine hydrate to form the corresponding hydrazone, 3,4,3',4'-tetramethoxy-6-(1-ethyl-2-hydrazono-propyl) benzophenone. The hydrazone is then cyclized in the presence of methanol (MeOH) and gaseous hydrogen chloride to yield racemic tofisopam. See, U.S. Pat. Nos. 3,736,315 and 6,080,736, the entire disclosure of which are incorporated herein by reference. The synthetic route to racemic tofisopam is depicted below:

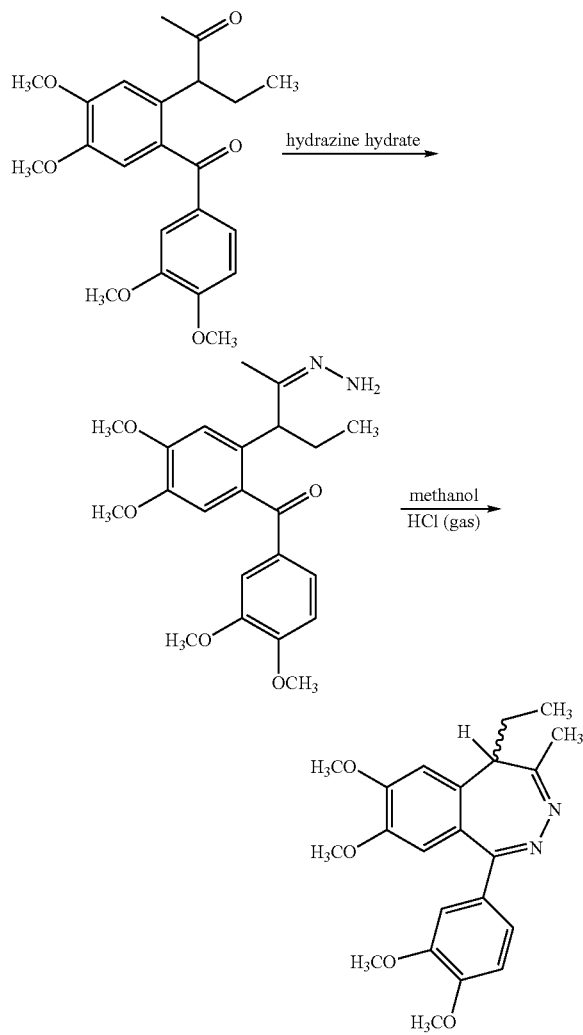

The main impurities in the product resulting from the above reaction are the starting 3,4,3',4'-tetramethoxy-6-(α-aceto-propyl)benzophenone and the hydrazone intermediate.

The resolution of tofisopam by chiral chromatography using macrocyclic glycopeptide as a stationary phase on a Chirobiotic V™ column (ASTEAC, Whippany, N.J.) and using 10% MeOH in tert-butylmethyl ether as the mobile phase, is disclosed in U.S. Pat. No. 6,080,736. In this method, the (R)-(+) enantiomer was the first compound to elute from the column. (R)-(−)-tofisopam, (S)-(−/+) tofisopam, and residual (R)-(+)-tofisopam co-eluted and were collected in a subsequent fraction. Fitos et al. (*J. Chromatogr.*, 709 265 (1995)), discloses another method for resolving racemic tofisopam by chiral chromatography using a chiral α₁-acid glycoprotein as a stationary phase on a CHIRAL-AGP™ column (ChromTech, Cheshire, UK), and 10% ACN in a pH 7.0 phosphate buffer as the mobile phase. Zsila et al., disclose another resolution of tofisopam using Chiralcel® OJ® (Daicel) as a stationary phase and n-hexane, 2-propanol and MeOH (72:1.5:3) as a mobile phase, in a method taking more than 40 minutes to elute the enantiomers.

None of the disclosed methods has been optimized for production of large quantities of (R)-tofisopam of a chemical and enantiomeric purity suitable for preparation of a drug formulation. What is needed is an industrially applicable procedure for isolation of (R)-tofisopam, substantially free of the (S)-enantiomer of tofisopam, which:

(a) provides high chemical purity;
(b) provides high enantiomeric purity;
(c) provides high yield of the (R)-tofisopam; and
(d) provides the above features in an economically feasible process.

SUMMARY OF THE INVENTION

In one embodiment of the present invention there is provided a method of isolating (R)-tofisopam, substantially free of the (S)-enantiomer of tofisopam, said method comprising:

(a) adsorbing a mixture of enantiomers of tofisopam onto a chiral separation medium;

(b) passing a solvent system through the chiral separation medium in an amount sufficient to elute the tofisopam enantiomers from the separation medium;

(c) isolating the (R)-enantiomer of tofisopam, substantially free of the (S)-enantiomer of tofisopam;

wherein said chiral separation medium comprises:

(2S)-2-{(1S)[(3,5-dinitrophenyl)carbonylamino]phenylmethyl}-3,3-dimethylbutanoate covalently bound to silica; or an amylose derivative of formula I:

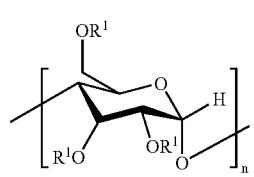

wherein each $R^1$ is a radical of the formula II:

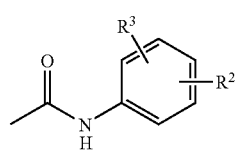

wherein $R^2$ and $R^3$ are independently selected from the group consisting of chloro and —$CH_3$; and n is an integer from about 2 to about 250, preferably from about 10 to about 150; more preferably from about 10 to about 100;

said amylose derivative coated on a porous inorganic carrier or a porous organic carrier.

In a sub-embodiment of the invention, the chiral separation medium comprises an amylose derivative wherein $R^2$ and $R^3$ are substituted on the radical of formula II in a substitution pattern selected from the group consisting of 3,4-dimethyl, 2,5-dimethyl, 3,4-dichloro, 2,5-dichloro, 5-chloro-2-methyl, 2-chloro-5-methyl, 4-chloro-3-methyl, 3-chloro-4-methyl, 3-chloro-2-methyl, 4-chloro-2-methyl, 2-chloro-6-methyl and 2-chloro-4-methyl.

Preferably, $R^2$ and $R^3$ are substituted on the radical of formula II in a substitution pattern selected from the group consisting of 5-chloro-2-methyl and 3-chloro-4-methyl.

In one preferred sub-embodiment, said chiral separation medium comprises an amylose derivative of formula Ia:

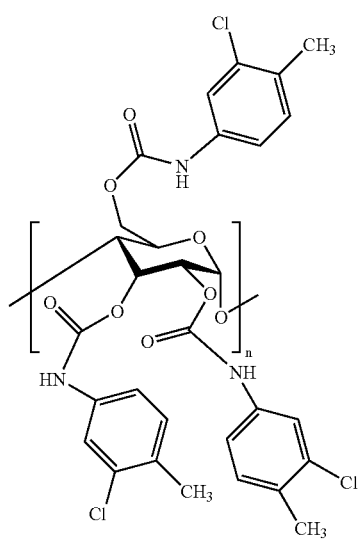

Ia wherein n is an integer from about 2 to about 250, preferably from about 10 to about 150; more preferably from about 10 to about 100;

said amylose derivative coated on a porous inorganic carrier or a porous organic carrier.

In one embodiment of the invention, there is provided a method of isolating the (+)-conformer of (R)-tofisopam, substantially free of the (S)-enantiomer of tofisopam, said method comprising:

(a) providing a chromatography column packed with a chiral separation medium comprising:
  (2S)-2-{(1S)[(3,5-dinitrophenyl)carbonylamino]phenylmethyl}-3,3-dimethylbutanoate covalently bound to silica; or
  an amylose derivative of formula I or formula Ia as defined above;

(b) providing a flow of a solvent system through said column;

(c) adsorbing a mixture of tofisopam enantiomers, preferably dissolved in the solvent system, onto the chiral separation medium;

(d) passing a first amount of the solvent system through the chromatography column sufficient to elute from said chiral separation medium substantially all of the (S)-enantiomer of tofisopam present in the mixture of tofisopam enantiomers, substantially free of the (+)-conformer of (R)-tofisopam; and (e) passing a second amount of the solvent system through the chromatography column, sufficient to elute from the chiral separation medium the (+)-conformer of (R)-tofisopam substantially free of the (S)-enantiomer of tofisopam.

In one embodiment, steps (c) to (e) are completed in less than about 25 minutes, preferably from about 18 to about 22 minutes.

In some embodiments, the mixture of tofisopam enantiomers to be resolved may be a racemic mixture. In other embodiments, the mixture of tofisopam enantiomers may be other than a racemic mixture.

In some embodiments, the solvent system is isocratic throughout the chromatographic separation. In other embodiments, the solvent system may comprise a gradient from a first solvent composition to a second composition.

In some embodiments of the invention, the chiral separation medium is contained in a chromatography column.

In some embodiments of the invention, the chiral separation medium is contained in a plurality of chromatography columns. In one sub-embodiment thereof, the chiral separation medium is contained in a moving bed. In another sub-embodiment thereof, the chiral separation medium is contained in a simulated moving bed.

In one sub-embodiment, the chiral separation medium is present in the chromatography column in an amount from about 300 to about 350 kg.

In another sub-embodiment thereof, the rate of flow of the solvent system through the chromatography column is from about 7,000 to about 8,000 liters per hour.

In another sub-embodiment thereof, the chiral separation medium is present in the chromatography column in an amount sufficient to resolve, in a single batch, an amount of racemic tofisopam from about 5 to about 7 kg.

In one sub-embodiment thereof, the (R)-enantiomer of tofisopam, substantially free of the (S)-enantiomer of tofisopam, is isolated in a yield of at least about 65%, preferably at least about 70%, more preferably at least about 75%, even more preferably at least about 85%.

In another sub-embodiment thereof, the (R)-enantiomer of tofisopam, substantially free of the (S)-enantiomer of tofisopam, is isolated in an enantiomeric purity of greater than 98% enantiomeric excess.

In another sub-embodiment thereof, the amount of said solvent system necessary to isolate the (R)-enantiomer of tofisopam, substantially free of the (S)-enantiomer, is from about 1300 to about 1400 liters per kilogram of (R)-tofisopam.

In one embodiment of the invention, the chiral separation medium comprises an amylose derivative of formula I, and the solvent system comprises acetonitrile (ACN). In a sub-embodiment thereof, the solvent system comprises a mixture comprising ACN and an alkyl alcohol.

Suitable organic carriers for supporting the amylose derivative of formula I or formula Ia include, for example polystyrene, polyacrylamide and polyacrylate. Suitable porous inorganic carriers for supporting the amylose deriva tive of formula I include, for example, silica, alumina, magnesia, glass, kaolin, titanium oxide and silicates. The carrier for supporting the amylose derivative of formula I or formula Ia comprises a particle size of from about 10 to about 100 microns, preferably from about 10 to about 50 microns, more preferably from about 10 to about 30 microns, most preferably about 20 microns.

In another embodiment of the invention, the chiral separation medium comprises (2S)-2-{(1S)[(3,5-dinitrophenyl) carbonylamino]phenylmethyl}-3,3-dimethylbutanoate covalently bound to silica, and the solvent system comprises a mixture of a hydrocarbon solvent and an alkyl alcohol. The silica to which the (2S)-2-{(1S)[(3,5-dinitrophenyl)carbonylamino]phenylmethyl}-3,3-dimethylbutanoate is covalently bound comprises a particle size of from about 10 to about 100 microns, preferably from about 10 to about 50 microns, more preferably from about 10 to about 30 microns, most preferably about 20 microns.

In another embodiment of the invention, there is provided an (R)-enantiomer of tofisopam substantially free of (S)-enantiomer of tofisopam, said (R)-enantiomer having an enantiomeric excess of greater than 98%.

In another embodiment of the invention, there is provided a pharmaceutical composition comprising a pharmaceutically acceptable carrier and an (R)-enantiomer of tofisopam substantially free of (S)-enantiomer of tofisopam; said (R)-enantiomer having an enantiomeric excess of greater than 98%.

DETAILED DESCRIPTION OF THE INVENTION

Figure 1:
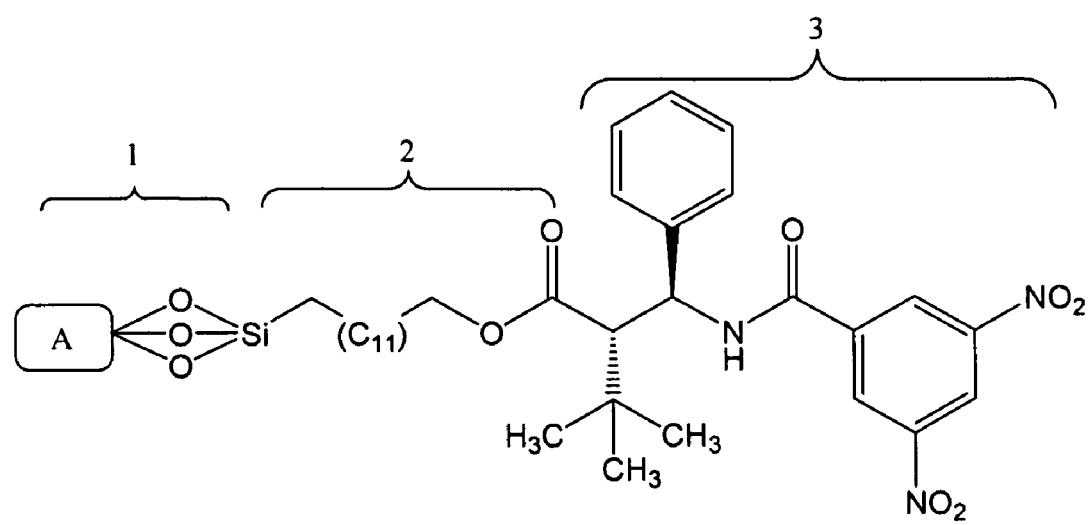
FIG. 1 shows the covalent linkage of the chiral functionality to the silica carrier, A, in (S,S)-β-GEM.

A selection of chiral separation media were experimentally assessed for use in the resolution of tofisopam. It was found that most of the experimental separations were unsatisfactory because the chiral separation media were either incapable of providing satisfactory resolution of tofisopam enantiomers, or demonstrated long retention times when optimized to resolve the tofisopam enantiomers.

Retention time for the (R)-enantiomer of tofisopam is a significant factor in resolution of tofisopam enantiomers. This is because the (R)-enantiomer in solution demonstrates an equilibrium between the (R)-(+) and (R)-(−) conformers. The equilibrium composition of (R)-tofisopam in solution is about 85% of the (R)-(+) conformer and about 15% of the (R)-(−) conformer. The equilibration continues during chromatographic separation. As the tofisopam enantiomers and conformers resolve from the mixture on the separation medium, they form areas of purified single isomers, referred to as "bands" that move with the flow of the solvent system. The major (R)-enantiomer conformer, (R)-(+), is retained most by the separation medium, and the (R)-(−), conformer is retained least. Throughout the separation, the major (R)-(+)-conformer equilibrates at a finite rate to the minor (R)-(−) conformer. This results in broadening of the bands and may serve to significantly lower yields of (R)-tofisopam isolated via chromatographic resolutions. Thus, separation conditions that achieve resolution of (R)-tofisopam in a shorter time interval are advantageous because the equilibration of the conformers of (R)-tofisopam as a function of time is minimized, and the yield of the major conformer of (R)-tofisopam is increased.

The present invention provides a chiral chromatographic method for isolating (R)-tofisopam, substantially free of the (S)-enantiomer of tofisopam, via chromatographic resolution of a mixture of tofisopam enantiomers. The method of the present invention is applicable to small scale samples for analytical applications and is particularly useful in the preparation of large quantities of (R)-tofisopam. The method is rapid, high yielding, and provides (R)-tofisopam of high chemical and high enantiomeric purity. The method may be used for resolving racemic mixtures of tofisopam enantiomers and tofisopam mixtures other than racemic mixtures, for example partially resolved tofisopam. The tofisopam feed for the method may contain additional contaminants other than the (R)- and (S)-enantiomers and their respective conformers. Such additional contaminants may include, for example, synthetic intermediates in the tofisopam synthesis.

The expression "separation medium" means the material on which a mixture of components to be separated is differentially adsorbed during a chromatographic separation. This material is often referred to as a "stationary phase" when chromatographic separation is performed in a chromatography column.

The expression "chiral separation medium" means that the separation medium comprises a chiral functionality such that the separation medium may interact differently with the two enantiomers of an optically active compound.

The expression "solvent system" means the solvent, or mixture of solvents, which elutes a mixture of components to be separated from a separation medium on which the mixture of components is differentially adsorbed. In conventional column chromatography, this material is referred to as a "mobile phase."

The terms "adsorb" and "adsorption" refer to an interaction between the separation medium and a component of a mixture to be separated by chromatography on the separation medium. The forces involved are relatively small, on the order of van der Waals forces.

The term "isocratic" means that the composition of the solvent system remains constant throughout the chromatographic method.

The term "gradient," when used as a parameter in chromatographic separation, means that the composition of the solvent system is varied according over at least one time interval during the chromatographic method. The gradient may be linear or may be stepped.

The expression "adsorption constant" and the symbol $\overline{K}$ describe the degree to which a compound is retained by a separation medium in a chromatographic separation. The adsorption constant for a compound "a" in a dilute single-component system is equal to the ratio of the concentration of [a] in the mobile phase (solvent system) $C_a$ (g/l) to the concentration of [a] in the stationary phase (separation medium) $\overline{C}_a$ (g/l). In the case of a multi-component system, the different components compete with each other for the finite number of adsorption sites on the separation medium. Thus, the concentration of a given species [a] depends not only on its mobile phase concentration, but also on the mobile phase concentration of all other components in the system.

For a mixture of two components (A and B) at low concentration, the retention times $t_R(A)$ and $t_R(B)$ are related to the adsorption constants according to:

$$\overline{K}_A = \frac{t_R(A) - t_0}{t_0} \cdot \frac{\varepsilon_E}{1 - \varepsilon_E}$$

$$\overline{K}_B = \frac{t_R(B) - t_0}{t_0} \cdot \frac{\varepsilon_E}{1 - \varepsilon_E}$$

wherein:

the term $\varepsilon_E$ is the "external porosity," defined as $V_{ML}/V_{COL}$, where $V_{ML}$ is the volume of moving (non-stagnant) mobile phase and $V_{COL}$ is the volume of the chromatography column; and the term $t_0$ is the "zero retention time" defined by the expression:

$$t_0 = \frac{\varepsilon_E * V_{COL}}{Q}$$

wherein Q is the flow rate of the mobile phase. Thus for a 250 mm×4.6 mm chromatography column, operated at a flow rate of 1 mL/min, with an external porosity of 0.4, the calculated zero retention time is:

$$t_0 = \frac{\varepsilon_E * V_{COL}}{Q} = \frac{0.4 * 4.15}{1} = 1.66 \text{ min}$$

The term "selectivity" between two components on a separation medium is a measure of the degree to which two components are resolved in a chromatographic separation. Selectivity is symbolized as "α" and is defined as the ratio of the respective retention factors of the two components:

$$\alpha = \frac{\overline{K}_A}{\overline{K}_B} = \frac{\overline{C}_A / C_B}{\overline{C}_B / C_A}$$

The expression "optically active" refers to a property whereby a material rotates the plane of plane-polarized light. A compound that is optically active is nonsuperimposable on its mirror image. The property of nonsuperimposablity of an object on its mirror image is called chirality.

The property of "chirality" in a molecule may arise from any structural feature that makes the molecule nonsuperimposable on its mirror image. The most common structural feature producing chirality is an asymmetric carbon atom, i.e., a carbon atom having four nonequivalent groups attached thereto.

The term "enantiomer" refers to each of the two nonsuperimposable isomers of a pure compound that is optically active. Single enantiomers are designated according to the Cahn-Ingold-Prelog system, a set of priority rules that rank the four groups attached to an asymmetric carbon. See March, Advanced Organic Chemistry, 4$^{th}$ Ed., (1992), p. 109. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example below, the Cahn-Ingold-Prelog ranking sequence id A>B>C>D. The lowest ranking atom, D is oriented away from the viewer.

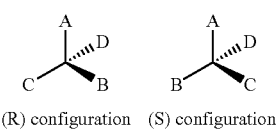

(R) configuration   (S) configuration

The term "racemate" or the phrase "racemic mixture" refers to a 50-50 mixture of two enantiomers such that the mixture does not rotate plane-polarized light.

The expression "enantiomeric excess," generally reported as a percentage, is a means of expressing the degree of enantiomeric purity of a non-racemic mixture, ie., a resolved or partially resolved enantiomer. The percent enantiomeric excess (% e.e.) is defined as:

$$\% \text{ enantiomeric excess} = \frac{[R]-[S]}{[R]+[S]} \times 100 = \%R - \%S$$

The expression "(R)-tofisopam, substantially free of the (S)-enantiomer of tofisopam," means a composition that comprises at least about 80% e.e. of the (R)-enantiomer of tofisopam. Preferably, such a composition comprises at least about 90% e.e. of the (R)-enantiomer of tofisopam. More preferably, such a composition comprises at least about 95% e.e. of the (R)-enantiomer of tofisopam. Most preferably, such a composition comprises greater than 98% e.e. of the (R)-enantiomer of tofisopam.

The term "linker," when used to describe a chiral separation medium, refers to the functional group that serves as a tether to link the chiral functionality to a carrier such as silica. One example, shown in FIG. 1, is the alkylene ester linker 2 that forms the covalent linkage of the chiral functionality 3 of commercially available (S,S)-β-GEM to the silica carrier 1.

The Chiral Separation Media

The method of the invention employs a chiral separation medium which comprises (2S)-2-{(1S)[(3,5-dinitrophenyl)carbonylamino]phenylmethyl}-3,3-dimethylbutanoate covalently bound to silica, or an amylose derivative of formula I, coated on a porous inorganic carrier or a porous organic carrier.

The covalent bond between the (2S)-2-{(1S)[(3,5-dinitrophenyl)carbonylamino]phenylmethyl}-3,3-dimethylbutanoate and the silica preferably comprises an alkylene ester linkage, wherein the alkylene portion of the linkage is preferably a $C_8$-$C_{18}$ alkylene, more preferably a $C_{10}$-$C_{15}$ alkylene, most preferably a $C_{13}$ alkylene. One example of a chiral separation medium comprising a (2S)-2-{(1S)[(3,5-dinitrophenyl)carbonylamino]-phenylmethyl}-3,3-dimethylbutanoate is the commercially available product (S,S)-β-GEM, manufactured by Regis Technologies, 8210 Austin Avenue, Morton Grove, Ill. 60053.

Chiral separation media comprising amylose derivatives are disclosed in U.S. Pat. No. 5,202,433, the entire disclosure of which is incorporated herein by reference. Several examples of chiral separation media comprising an amylose derivative of formula I, are disclosed by Chankvetadze et al., *J. Chromatography A*, 694 (1995), pp 101-109, the entire disclosure of which is incorporated herein by reference.

Synthesis of phenyl carbamate derivatives of amylose according to formula I may be carried out by reacting amylose with an amount of a phenyl isocyanate substantially in excess of the stoichiometric amount required to completely react the free hydroxy groups of amylose, in the presence of an acid scavenger such as, for example pyridine. See, Chankvetadze et al., Id at page 102. The derivatized amylose may be coated onto a porous organic or inorganic support, by methods known in the art. See, Okamoto et al., *J. Chromatography*, 363 (1986), pg. 106, the entire disclosure of which is incorporated herein by reference. The amylose derivative, coated on a porous support may be packed in a chromatography column using dry packing or slurry packing methods known in the art.

The chiral separation medium may be packed in a chromatography column, and the solvent system passed through the column.

The method of the invention is applicable to both batch and continuous chromatography. Batch-mode separations may be carried out on a single high capacity chromatography column. Continuous separations may be carried out on multiple linked columns. The columns may comprise stationary columns, moving beds or simulated moving beds. Simulated moving bed techniques for chromatographic separations are described, for example, in U.S. Pat. Nos. 5,434,298, 5,434,299, 5,498,752, 5,635,072, 5,518,625, and 6,458,955, the entire disclosure of which are incorporated herein by reference.

The Solvent System

When the separation medium is (2S)-2-{(1S)[(3,5-dinitrophenyl)carbonylamino]phenylmethyl}-3,3-dimethylbutanoate covalently bound to silica, the solvent system preferably comprises a mixture comprising a hydrocarbon solvent and an alkyl alcohol. The alkyl alcohol is preferably a ($C_1$-$C_4$) alcohol, more preferably ethanol (EtOH). The hydrocarbon solvent is preferably a ($C_5$-$C_{10}$) hydrocarbon, most preferably heptane. According to particularly preferred embodiments of the invention, the solvent composition comprises from about 25% to about 60% EtOH in heptane (V/V), preferably from about 35% to about 50% EtOH in heptane (V/V), more preferably about 40% EtOH in heptane (V/V).

When the separation medium is an amylose derivative of formula I, coated on a porous inorganic carrier or a porous organic carrier, the solvent system preferably comprises a mixture of ACN and an alkyl alcohol. The alkyl alcohol is preferably a ($C_1$-$C_4$) alcohol. The alcohol is most preferably MeOH. The solvent system preferably comprises from about 5% (V/V) to about 40% (V/V) MeOH in ACN, more preferably from about 10% (V/V) to about 35% (V/V) MeOH in ACN, even more preferably from about 15% (V/V) to about 25% (V/V) MeOH in ACN, most preferably about 19% (V/V) MeOH in ACN.

The addition of an alkyl alcohol to the ACN solvent system is observed to have a significant effect on the resolution of tofisopam. All four isomers of tofisopam are resolved. However, though selectivity is improved between the enantiomers of tofisopam and their respective conformers, the solubility of tofisopam decreases with higher concentrations of alkyl alcohol in the solvent system. Thus the concentration of an alkyl alcohol in the solvent system is preferably no more than about 40% by volume.

Solubility studies have determined that the solubility of racemic tofisopam in a mixture of 19% (V/V) MeOH in ACN is about 135.5 g/L. Thus, in an embodiment of the invention wherein the solvent system comprises about 19% (V/V) MeOH in ACN, the concentration of the feed of tofisopam is limited to a concentration of less than 135.5 g/L. Preferably, the concentration of the feed of a mixture of enantiomers of tofisopam in the practice of the invention is from about 80 to about 120 g/L, most preferably about 100 g/L.

The solvent systems employed in the practice of the invention may be isocratic or may comprise a gradient from one solvent composition to another solvent composition over one or more time intervals during the chromatographic separation. Preferably the solvent system is isocratic.

Preparative Scale Resolutions

The isolation method of the present invention is particularly suited to preparative scale resolution of enantiomeric mixtures of tofisopam. The method of the invention is useful for resolving tofisopam under overloading conditions, i.e., amounts of tofisopam high enough to interact with all adsorption sites in the upstream portion of the separation medium, as well as with separations of dilute solutions, i.e., non-overloading conditions, such as analytical scale separations of tofisopam.

The temperature under which the chromatographic resolution is performed may conveniently be controlled by maintaining the separation medium is a controlled temperature environment and/or maintaining a controlled temperature for the solvent system flowing through the separation medium. The preferred temperature range for chromatographic resolutions in the practice of the invention is from about 5° C. to about 40° C., preferably from about 20° C. to about 30° C., most preferably about 25° C.

The solvent composition of the solvent system, the flow rate of the solvent system through the resolution medium, and the amount of the separation medium are factors which contribute to the time required for the resolution of a mixture of enantiomers of tofisopam in the practice of the method of the invention. Preferably, the chromatographic separation is completed in from about 15 to about 25 minutes, more preferably from about 18 to about 22 minutes.

Isolated (R)-Tofisopam

The method of the invention allows the isolation of the (R)-enantiomer of tofisopam, substantially free of the (S)-enantiomer of tofisopam.

The (R)-enantiomer of tofisopam isolated by the method of the present invention may be further formulated in a pharmaceutical composition, in combination with a pharmaceutically acceptable carrier. The active ingredient in such formulations may comprise from 0.1 to 99.99 weight percent. By "pharmaceutically acceptable carrier" is meant any carrier, diluent or excipient which is compatible with the other ingredients of the formulation and is not deleterious to the recipient.

For use in therapy, the (R)-enantiomer of tofisopam isolated by the method of the present invention is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences*, 18th Ed., (1990) Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water-soluble salt of the active agent. Stabilizing agents, antioxidizing agents and preservatives may also be added. Suitable antioxidizing agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or nonaqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The compositions of the present invention can also be formulated so as to provide slow or controlled-release of the active ingredient therein. In general, a controlled-release preparation is a composition capable of releasing the active ingredient at the required rate to maintain constant pharmacological activity for a desirable period of time. Such dosage forms can provide a supply of a drug to the body during a predetermined period of time and thus maintain drug levels in the therapeutic range for longer periods of time than other non-controlled formulations.

For example, U.S. Pat. No. 5,674,533 discloses controlled-release compositions in liquid dosage forms for the administration of moguisteine, a potent peripheral antitussive. U.S. Pat. No. 5,059,595 describes the controlled-release of active agents by the use of a gastro-resistant tablet for the therapy of organic mental disturbances. U.S. Pat. No. 5,591,767 discloses a liquid reservoir transdermal patch for the controlled administration of ketorolac, a non-steroidal anti-inflammatory agent with potent analgesic properties. U.S. Pat. No. 5,120,548 discloses a controlled-release drug delivery device comprised of swellable polymers. U.S. Pat. No. 5,073,543 discloses controlled-release formulations containing a trophic factor entrapped by a ganglioside-liposome vehicle. U.S. Pat. No. 5,639,476 discloses a stable solid controlled-release formulation having a coating derived from an aqueous dispersion of a hydrophobic acrylic polymer. The patents cited above are incorporated herein by reference.

The (R)-tofisopam used in the compositions of the present invention may take the form of a pharmaceutically-acceptable salt. The term "salts", in the context of a salt of (R)-tofisopam embraces salts commonly used to form addition salts of free bases. The term "pharmaceutically-acceptable salt" refers to salts that possess toxicity profiles within a range so as to have utility in pharmaceutical applications. Suitable pharmaceutically-acceptable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, aralphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, beta-hydroxybutyric, salicyclic, galactaric and galacturonic acid.

All of these salts may be prepared by conventional means, by reacting the appropriate acid with (R)-tofisopam, as isolated by the method of the present invention.

The practice of the invention is illustrated by the following non-limiting examples.

EXAMPLES

Example 1

Comparison of Different Chiral Stationary Phases Using Dilute Solutions Of Racemic Tofisopam Chromatographic separations of racemic tofisopam in dilute solution were conducted using the chiral separation media listed in Table 1. All of the separation media were packed in 4.6 mm (i.d.)×250 mm chromatography columns.

TABLE 1

| Functionality on the chiral separation media | Chemical structure of the chiral functionality | Tradename/ Manufacturer |
| --- | --- | --- |
| Amylose tris(3,5-dimethylphenylcarbamate) (coated on silica gel) | [structure] | Chiralpak ® AD ®, 20 μm, 1000 Å Chiral Technologies |
| Cellulose tris(3,5-dimethylphenylcarbamate) (coated on silica gel) | [structure] | Chiralcel ® OD ® 20 μm, 1000 Å Chiral Technologies |

TABLE 1-continued

| Functionality on the chiral separation media | Chemical structure of the chiral functionality | Tradename/ Manufacturer |
| --- | --- | --- |
| Cellulose tris(4-methybenzoate) (coated on silica gel) | | Chiralcel ® OJ ® 20 μm, 1000 Å Chiral Technologies |
| Amylose tris[(S)-α-methylbenzylcarbamate] (coated on silica gel) | | Chiralpak ® AS ®, 10 μm, 1000 Å Chiral Technologies |
| amylose derivative of formula Ia: (coated on silica gel) | | — |

TABLE 1-continued

| Functionality on the chiral separation media | Chemical structure of the chiral functionality | Tradename/ Manufacturer |
|---|---|---|
| sodium magnesium silicate particles, containing an optically-active ruthenium complex | 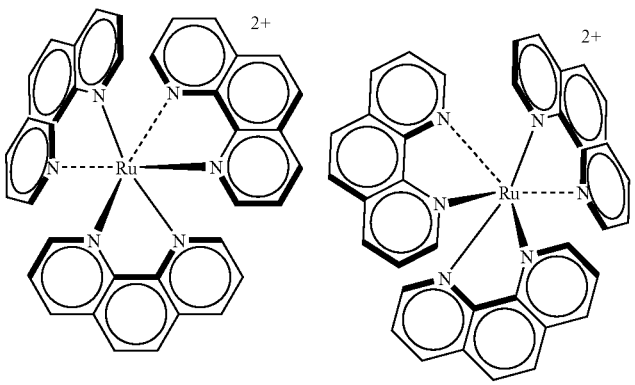<br>Optically active ruthenium complex contained in sodium magnesium silicate particles | Shiseido RU-1, 5 μm<br>Shiseido Fine Chemicals |
| O,O'-bis(3,5-dimethylbenzoyl)-N,N'-diallyl-L-tartardiamide polymer network covalently bonded to silica. | 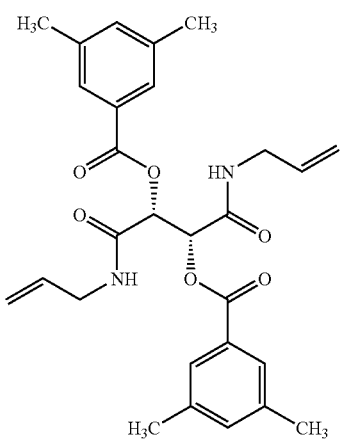<br>tartardiamide monomer comprising the polymer network | Kromasil ®<br>CHI-DMB, 10 μm, 100 Å<br>EKA Chemicals |
| O,O'-bis(4-tert-butylbenzoyl)-N,N'-diallyl-L-tartardiamide polymer network covalently bonded to silica. | 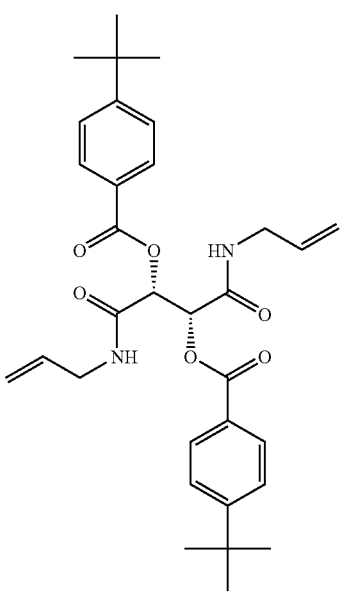<br>tartardiamide monomer comprising the polymer network | Kromasil ®<br>CHI-TBB, 10 μm, 100 Å<br>EKA Chemicals |

TABLE 1-continued

| Functionality on the chiral separation media | Chemical structure of the chiral functionality | Tradename/ Manufacturer |
| --- | --- | --- |
| (3R,4R)-4-(3,5-dinitrobenzamido)-1,2,3,4-tetrahydrophenanthrene | | (R,R)-Whelk-O ®, 10 μm, 100 Å Regis Technologies |
| 3,5-dinitrobenzoyl D-phenylglycine | | D-phenylglycine, 5 μm, 100 Å Regis Technologies |
| 3,5-dinitrobenzoyl derivative of 1,2-diaminocyclohexane | R = H, 3,5-dinitrobenzoyl | (R,R) DACH DNB, 5 μm, 100 Å Regis Technologies |
| N-(1-naphthyl) L-leucine (11-[(2R)-4-methyl-2-(naphthylamino) pentanoyloxy) | | L-Naphthylleucine, 5 μm, 100 Å Regis Technologies |
| N-tert-butylaminocarbonyl-L-leucineamido covalently bonded to silica through an amino propyl linkage | | BAC-L-leucine, 5 μm, 100 Å Regis Technologies |

TABLE 1-continued

| Functionality on the chiral separation media | Chemical structure of the chiral functionality | Tradename/ Manufacturer |
|---|---|---|
| N-{2-[(3,5-dinitrophenyl)carbonylamino]-1,2-diphenylethyl}decanamide covalently bonded to silica | 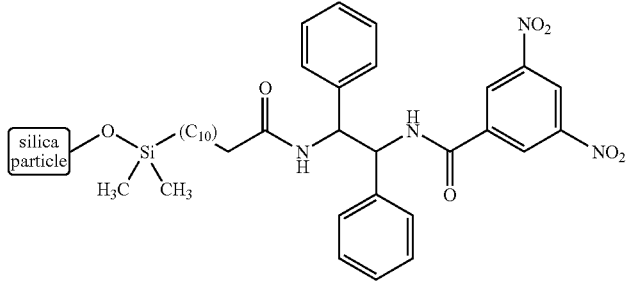 | (R,R) ULMO, 5 μm, 100 Å Regis Technologies |
| (2S)-2-{(1S)[(3,5-dinitrophenyl)carbonylamino]phenylmethyl}-3,3-dimethylbutanoate (covalently bound to silica through an alkylene ($C_{13}$) ester linkage | 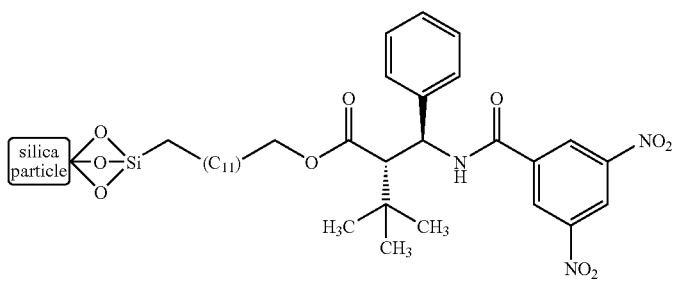 | (S,S) β GEM, 5 μm, 100 Å Regis Technologies |

Table 2 below, lists the chiral separation media, the solvent systems, the temperature and the flow rate employed for each chiral separation medium tested. Solvent systems were prepared using HPLC grade solvents obtained from E.M. Science.

The Table also summarizes retention factors for all components resolved in each chromatographic separation.

TABLE 2

| Chromatographic conditions | | | | Retention Factors | | | |
|---|---|---|---|---|---|---|---|
| solid phase | liquid phase | Temp. | flow | Peak 1 | Peak 2 | Peak 3 | Peak 4 |
| Chiralpak ® AD ® | 100% ACN | 22° C. | 1.0 mL/min | 1.00 | — | — | — |
| Chiralpak ® AD ® | 90/10 ACN/MeOH | 22° C. | 1.0 mL/min | 0.73 | 0.97 | — | — |
| Chiralpak ® AD ® | 80/20 ACN/MeOH | 22° C. | 1.0 mL/min | 0.64 | 0.89 | — | — |
| Chiralpak ® AD ® | 50/50 ACN/MeOH | 22° C. | 1.0 mL/min | 0.60 | 0.88 | — | — |
| Chiralcel ® OD ® | 100% ACN | 22° C. | 1.0 mL/min | 0.78 | 0.83 | — | — |
| Chiralcel ® OD ® | 90/10 ACN/MeOH | 22° C. | 1.0 mL/min | 0.80 | — | — | — |
| Chiralcel ® OD ® | 70/30 heptane/EtOH | 22° C. | 1.0 mL/min | 0.77 | 1.27 | — | — |
| Chiralcel ® OJ ® | 100% ACN | 22° C. | 1.0 mL/min | 0.63 | 0.70 | — | — |
| Chiralcel ® OJ ® | 90/10 ACN/MeOH | 22° C. | 1.0 mL/min | 0.67 | — | — | — |
| Chiralpak ® AS ® | 100% ACN | 22° C. | 1.0 mL/min | 0.68 | — | — | — |
| Chiralpak ® AS ® | 60/40 heptane/EtOH | 22° C. | 1.0 mL/min | 1.04 | — | — | — |
| Shiseido RU-1 | 100% MeOH | 30° C. | 1.0 mL/min | 7.82 | 6.45 | — | — |
| Shiseido RU-1 | 100% MeOH | 15° C. | 1.0 mL/min | 9.80 | 14.71 | — | — |
| Shiseido RU-1 | 100% MeOH | 40° C. | 1.0 mL/min | 6.38 | 7.32 | 8.64 | — |

TABLE 2-continued

| Chromatographic conditions | | | | Retention Factors | | | |
|---|---|---|---|---|---|---|---|
| solid phase | liquid phase | Temp. | flow | Peak 1 | Peak 2 | Peak 3 | Peak 4 |
| Shiseido RU-1 | 100% MeOH | 50° C. | 1.0 mL/min | 5.19 | 6.61 | — | — |
| Kromasil ® CHI-DMB | 60/40 heptane/EtOH | 22° C. | 2.0 mL/min | 0.47 | — | — | — |
| Kromasil ® CHI-TBB | 60/40 heptane/EtOH | 22° C. | 2.0 mL/min | 0.36 | 0.49 | — | — |
| (R,R) Whelk-O ® | 100% MeOH | 22° C. | 1.0 mL/min | 2.77 | 3.10 | — | — |
| (R,R) Whelk-O ® | 100% ACN | 22° C. | 1.0 mL/min | 3.77 | — | — | — |
| (R,R) Whelk-O ® | 60/40 heptane/EtOH | 22° C. | 2.0 mL/min | 7.06 | 8.41 | — | — |
| D-phenyl glycine | 60/40 heptane/EtOH | 22° C. | 2.0 mL/min | 0.75 | — | — | — |
| D-phenyl glycine | 20/80 heptane/EtOH | 22° C. | 2.0 mL/min | 0.53 | — | — | — |
| D-phenyl glycine | 100% EtOH | 22° C. | 1.0 mL/min | 0.52 | — | — | — |
| (R,R) DACH DNB | 100% ACN | 22° C. | 1.0 mL/min | 0.71 | — | — | — |
| (R,R) DACH DNB | 60/40 heptane/EtOH | 22° C. | 1.0 mL/min | 1.67 | 1.96 | 8.43 | — |
| L-naphthyl leucine | 60/40 heptane/EtOH | 22° C. | 1.0 mL/min | 0.70 | — | — | — |
| BAC-L-leucine | 60/40 heptane/EtOH | 22° C. | 2.0 mL/min | 0.47 | — | — | — |
| (R,R) ULMO | 60/40 heptane/EtOH | 22° C. | 1.0 mL/min | 1.35 | — | — | — |
| (S,S)-β-GEM | 60/40 heptane/EtOH | 25° C. | 1.0 mL/min | 2.89 | 3.62 | 5.03 | 13.15 |
| Amylose derivative of formula Ia | 60/40 ACN/MeOH | 22° C. | 1.5 mL/min | 0.83 | 1.00 | 2.13 | 4.27 |

Of the tested chiral separation media, two materials resolved racemic tofisopam into four separate peaks. These materials were:

(S,S)-β-GEM, a commercially available material comprising a (2S)-2-{(1S)[(3,5-dinitrophenyl)carbonylamino]phenylmethyl}-3,3-dimethylbutanoate covalently bound to silica through an alkylene ($C_{13}$) ester linkage; and a chiral separation medium comprising an amylose derivative of formula Ia:

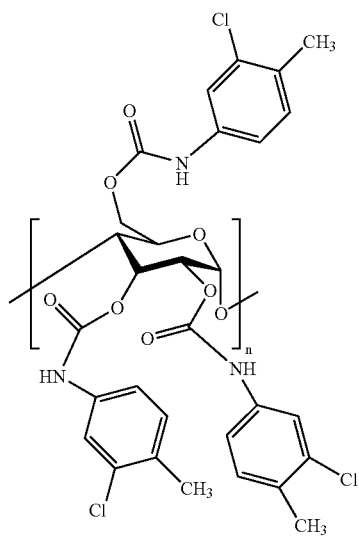

coated onto silica gel.

Separations were also observed for Chiralpak® AD®, Chiralcel® OD®, (R,R) Whelk-O®, and Shiseido RU-1. Chiralpak® AD® and Chiralcel® OD® exhibited poor resolution ($R_s$<0.5). The separation media, (R,R) Whelk-O®, and Shiseido RU-1 gave high retention constants that resulted in long retention times thus requiring substantially higher amounts of the solvent system.

Example 2

Determination of Elution Order of Tofisopam Enantiomers on a Chiral Separation Medium Comprising an Amylose Derivative of Formula Ia A 4.6 mm (i.d.)×250 mm chromatography column packed with a chiral separation medium, comprising an amylose derivative of formula Ia, was stabilized under conditions of: 100% ACN at a flow rate of 1.0 mL/min at 22° C. Racemic tofisopam (0.1 mg) was injected into the column, and fractions of the effluent were collected every 0.5 minutes between 1.5 and 6.0 minutes following the injection. These fractions were analyzed for the amounts of each of the four isomers of tofisopam. The data is plotted in FIG. 1, was constructed to show the peak profile of the resolution in 100% ACN.

Figure 3:
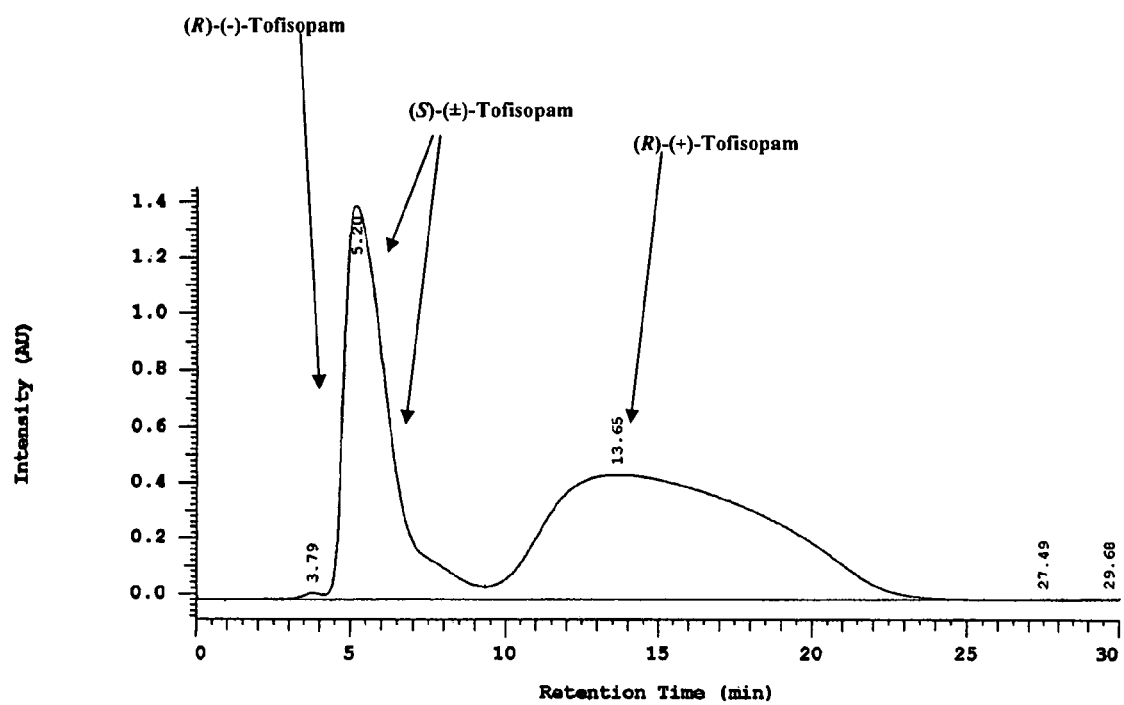
FIG. 3 shows a diagram of a chromatographic resolution of an overload injection of racemic tofisopam using a chiral separation medium comprising an amylose derivative of formula Ia and a solvent system comprising 100% ACN.

Tofisopam isomers were eluted in the following order: (R)-(−); (S)-(−)/(S)-(+); and (R)-(+). Due to the interconversion of the conformers during the chromatographic method, the presence of both the (R)-(−) and the (R)-(+) conformers is observed throughout the elution of the (S)-enantiomer.

amylose derivative of formula Ia, was stabilized under conditions of: 85/15 (V/V) ACN/MeOH at a flow rate of 1.6 mL/min at 25° C. A dilute injection of racemic tofisopam was injected. FIG. 3 shows the resulting separation.

Additional ACN/MeOH solvent compositions and the resulting resolution data are listed below in Table 3.

TABLE 3

| Conditions | | | Retention factors | | | | Selectivity $\alpha_1$ |
|---|---|---|---|---|---|---|---|
| liquid phase | Temp. | Flow mL/min | $\overline{K}_1$ (R)-(−) | $\overline{K}_2$ (S)-(−) | $\overline{K}_3$ (S)-(+) | $\overline{K}_4$ (R)-(+) | (S)-(+)/(R)-(+) |
| 100% ACN | 22° C. | 1.0 | — | — | 1.85 | 4.47 | 2.42 |
| 100% ACN | 40° C. | 2.0 | — | — | 1.24 | 2.87 | 2.32 |
| 80/20 ACN/MeOH | 22° C. | 2.0 | — | 1.03 | 2.16 | 4.11 | 1.90 |
| 77/23 ACN/MeOH | 22° C. | 1.5 | 0.88 | 1.04 | 2.26 | 4.28 | 1.90 |
| 60/40 ACN/MeOH | 22° C. | 1.5 | 0.83 | 1.00 | 2.13 | 4.27 | 2.00 |
| 70/30 ACN/MeOH | 22° C. | 1.5 | 0.91 | 1.23 | 2.85 | 6.76 | 2.37 |
| 81/19 ACN/MeOH | 25° C. | 1.1 | 0.85 | 1.02 | 2.18 | 4.12 | 1.89 |

Example 3

Figure 2:
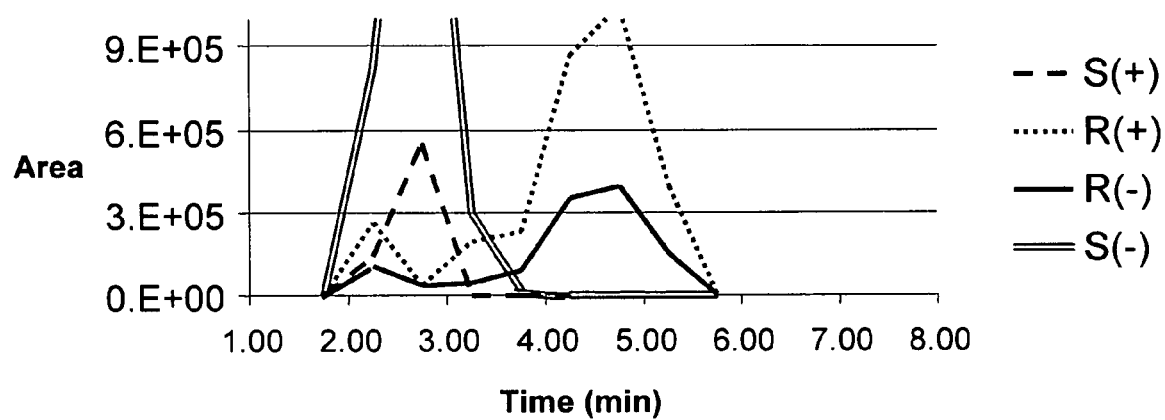
FIG. 2 shows a diagram of a reconstructed chromatographic resolution of racemic tofisopam using a chiral separation medium comprising an amylose derivative of formula Ia and a solvent system comprising 100% ACN, illustrating the elution order of the enantiomers of tofisopam.

Overload Injection of Racemic Tofisopam on a Chiral Separation Medium Comprising an Amylose Derivative of Formula Ia Eluted with 100% ACN A 4.6 mm (i.d.)×250 mm chromatography column packed with a chiral separation medium comprising an amylose derivative of formula Ia was stabilized under conditions of: 100% ACN at a flow rate of 1.0 mL/min at 25° C. Racemic tofisopam (300 µL at a concentration of 33 g/L) was injected into the column. FIG. 2 shows the resulting separation (UV detection at 345 nm). The yield of isolated (R)-tofisopam was approximately 60%. The measured enantiomeric excess (e.e.) of the (R)-tofisopam isolated in this separation was less than 95% e.e., due to the presence of the (S)-(+) enantiomer as a contaminant.

Example 4

Modification of the Solvent System: Resolution of Tofisopam on a Chiral Separation Medium Comprising an Amylose Derivative of Formula Ia Eluted with ACN/MeOH Mixtures Chromatographic separations of racemic tofisopam in dilute solution were conducted using a chiral separation medium comprising an amylose derivative of formula Ia, packed in a 4.6 mm (i.d.)×250 mm chromatography column. The solvent system was modified to compare resolution of tofisopam eluting with 100% ACN to resolution with ACN/MeOH mixtures wherein MeOH is present in a range of concentrations from about 5% to about 40%

A 4.6 mm (i.d.)×250 mm, chromatography column, packed with a chiral separation medium comprising an Selectivity between the enantiomers and their respective conformers of tofisopam was increased by the addition of MeOH to the solvent system.

Example 5

Overload Injection of Racemic Tofisopam on a Chiral Separation Medium Comprising an Amylose Derivative of Formula Ia Eluted with 85/15 ACN/MeOH (V/V)

Figure 4:
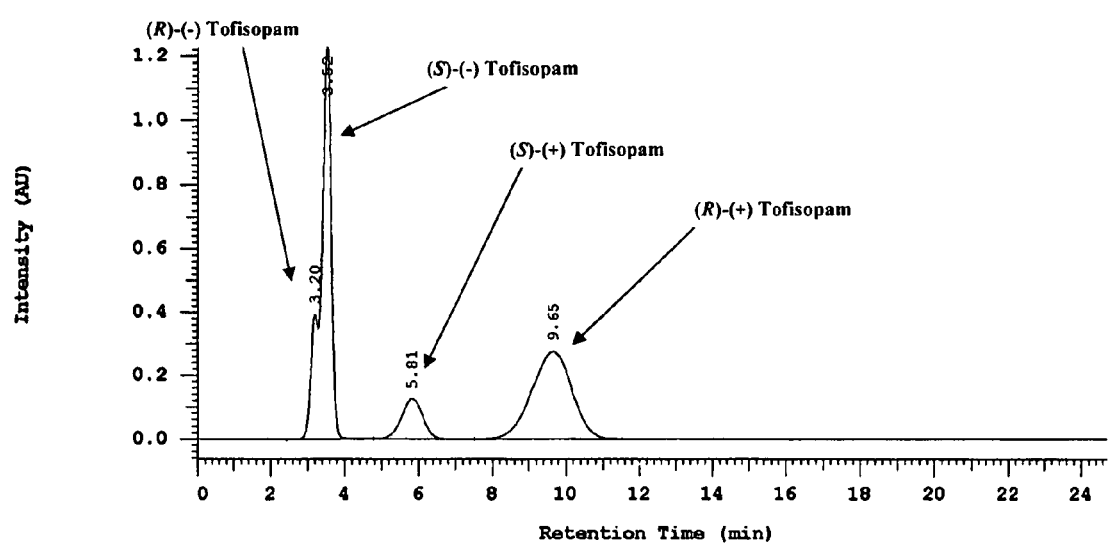
FIG. 4 shows a diagram of a chromatographic resolution of a dilute injection of racemic tofisopam using a chiral separation medium comprising an amylose derivative of formula Ia and a solvent system comprising 85% ACN/15% MeOH (V/V).

A 4.6 mm (i.d.)×250 mm, chromatography column, packed with a chiral separation medium comprising an amylose derivative of formula Ia, was stabilized under conditions of: 85/15 (V/V) ACN/MeOH at a flow rate of 1.0 mL/min at 25° C. Racemic tofisopam (9.9 mg was injected. FIG. 4 shows the resulting separation (UV detection at 345 nm). The vertical dotted line marks the cut point (11.6 min) where collection of (R)-(+)-tofisopam was commenced. Analysis of the fractions obtained from this overload experiment showed a yield of greater than 83%, and an enantiomeric excess greater than 98% for the (R)-enantiomer.

Example 6

Overload Injection of Racemic Tofisopam on a Chiral Separation Medium Comprising an Amylose Derivative of Formula Ia Eluted with 81/19 ACN/MeOH (V/V)

Figure 5:
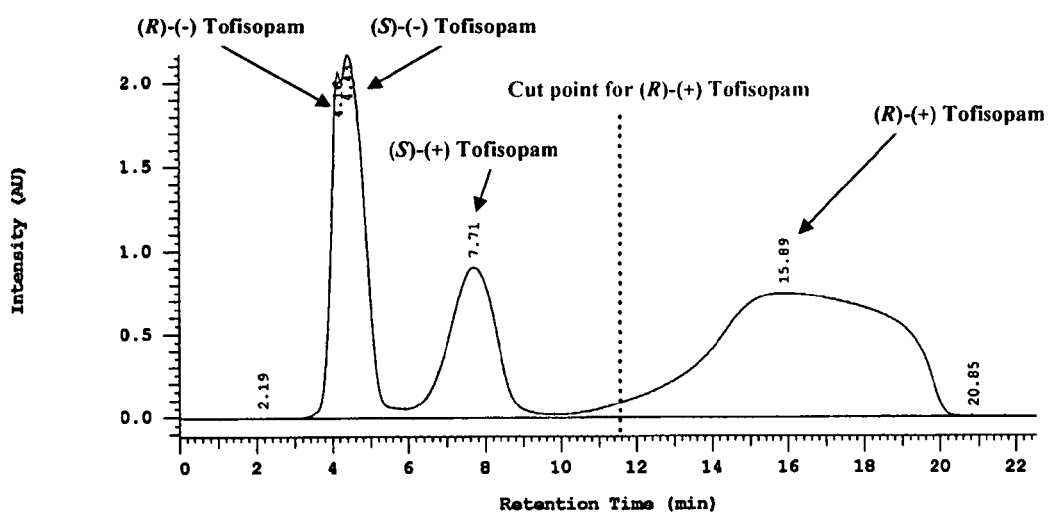
FIG. 5 shows a diagram of a chromatographic resolution of an overload injection of racemic tofisopam using a chiral separation medium comprising an amylose derivative of formula Ia and a solvent system comprising 85% ACN/15% MeOH (V/V).
Figure 6:
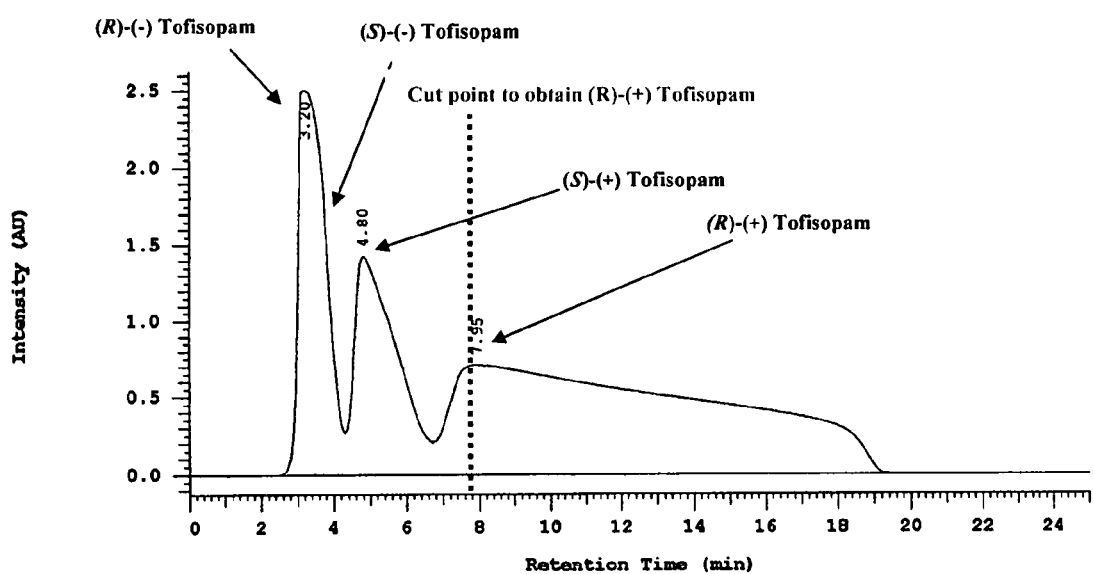
FIG. 6 shows a diagram of a chromatographic resolution of an overload injection of racemic tofisopam using a chiral separation medium comprising an amylose derivative of formula Ia and a solvent system comprising 81% ACN/19% MeOH (V/V) (V/V).

A 4.6 mm (i.d.)×250 mm, chromatography column packed with a chiral separation medium comprising an amylose derivative of formula Ia was stabilized under conditions of: 81/19 (V/) ACN/MeOH at a flow rate of 1.17 mL/min at 25° C. Racemic tofisopam (500 µL of a 104 g/L concentration) was injected. FIG. 5 shows the resulting separation (UV detection at 355 nm). The vertical dotted line marks the cut point (8.0 min) where collection of (R)-(+)-tofisopam was commenced. Analysis of the fractions obtained from this overload experiment showed a yield of approximately 73% and an enantiomeric excess greater than 98% for the (R)-enantiomer.

Higher concentrations of MeOH in the solvent system were observed to yield increased selectivity. However solubility of racemic tofisopam decreased with the higher concentrations of MeOH.

All references cited herein are incorporated by reference. The present invention may be embodied in other specific forms without departing from the spirit of essential attributes thereof and, accordingly, reference should be made to the appended claims, rather than to the foregoing specification, as indication of the scope of the invention.

What is claimed is:

1. A method of isolating (R)-tofisopam, substantially free of the (S)-enantiomer of tofisopam, said method comprising:
   (a) adsorbing a mixture of enantiomers of tofisopam onto a chiral separation medium;
   (b) passing a solvent system through the chiral separation medium in an amount sufficient to elute the tofisopam enantiomers from the separation medium;
   (c) isolating the (R)-enantiomer of tofisopam, substantially free of the (S)-enantiomer of tofisopam;
   wherein said chiral separation medium comprises:
   (2S)-2-{(1S)[(3,5-dinitrophenyl)carbonylamino]phenylmethyl}-3,3-dimethylbutanoate covalently bound to silica, or
   an amylose derivative of formula I:

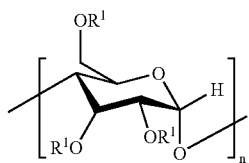

wherein each R¹ is a radical of the formula II:

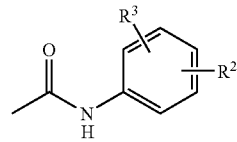

wherein R² and R³ are independently selected from the group consisting of chloro and —CH³ and are substituted on the radical of formula II in a substitution pattern selected from the group consisting of 3,4-dimethyl, 2,5-dimethyl, 3,4-dichloro, 2,5-dichloro, 5-chloro-2-methyl, 2-chloro-5-methyl, 4-chloro-3-methyl, 3-chloro-4-methyl, 3-chloro-2-methyl, 4-chloro-2-methyl, 2-chloro-6-methyl and 2-chloro-4-methyl; and
   n is an integer from about 10 to about 100;
   said amylose derivative coated on a porous inorganic carrier or a porous organic carrier.

2. The method of claim 1 wherein said separation medium comprises an amylose derivative of formula I.

3. The method of claim 2 wherein the substitution pattern on the radical of formula II is selected from the group consisting of 5-chloro-2-methyl and 3-chloro-4-methyl.

4. The method of claim 3 wherein said chiral separation medium comprises an amylose derivative of formula Ia:

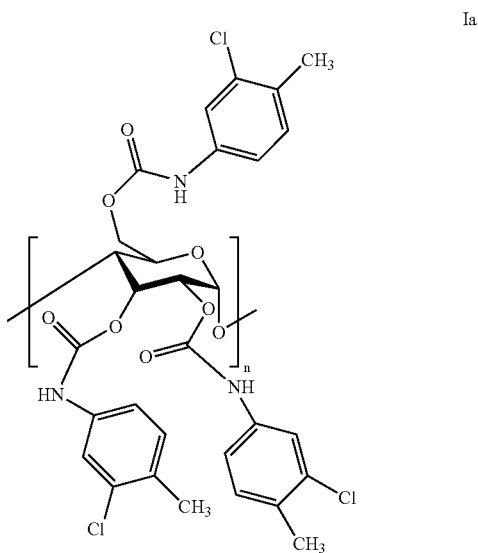

wherein n is an integer from about 10 to about 100.

5. The method of claim 1 wherein said solvent system comprises acetonitrile.

6. The method of claim 5 wherein said solvent system further comprises an alkyl alcohol.

7. The method of claim 6, wherein said alkyl alcohol is methanol.

8. The method of claim 7, wherein said methanol is present in said solvent system in an amount of from about 5 to about 40 volume percent.

9. The method of claim 8, wherein said methanol is present in said solvent system in an amount of from about 10 to about 35 volume percent.

10. The method of claim 9, wherein said methanol is present in said solvent system in an amount of from about 15 to about 25 volume percent.

11. The method of claim 10, wherein said methanol is present in said solvent system in an amount of about 19 volume percent.

12. The method of claim 1 wherein said chiral separation medium comprises (2S)-2-{(1S)[(3,5-dinitrophenyl)carbonylamino]-phenylmethyl}-3,3-dimethyl-butanoate covalently bound to silica.

13. The method of claim 12 wherein said solvent system comprises a mixture of heptane and an alkyl alcohol.

14. The method of claim 13, wherein said alkyl alcohol is ethanol.

15. The method of claim 14, wherein said ethanol is present in said solvent system in an amount of from about 25 to about 60 volume percent.

16. The method of claim 15, wherein said ethanol is present in said solvent system in an amount of from about 35 to about 50 volume percent.

17. The method of claim 16, wherein said ethanol is present in said solvent system in an amount of about 40 volume percent.

18. The method of claim 1 wherein the process is performed at a temperature of from about 5° C. to about 40° C.

19. The method of claim 18 wherein the process is performed at a temperature of about 25° C.

20. The method of claim 1 wherein said (R)-tofisopam is isolated in an enantiomeric excess of greater than 95%.

21. The method of claim 20 wherein said (R)-tofisopam is isolated in an enantiomeric excess of greater than 98%.

22. The method of claim 1 wherein the chiral separation medium is contained in a chromatography column.

23. A method of isolating the (R)-enantiomer of tofisopam, substantially free of the (S)-enantiomer of tofisopam, said method comprising:
(a) providing a chromatography column packed with a chiral separation medium comprising:
(2S)-2-{(1S)[(3,5-dinitrophenyl)carbonylamino]phenylmethyl}-3,3-dimethylbutanoate, covalently bound to silica through an alkylene ester linkage; or an amylose derivative of formula I:

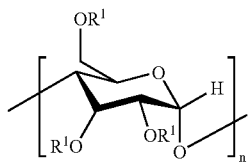

wherein each $R^1$ is a radical of the formula II:

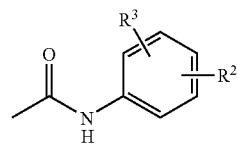

wherein $R^2$ and $R^3$ are independently selected from the group consisting of chloro and —$CH_3$ and are substituted on the radical of formula II in a substitution pattern selected from the group consisting of 3,4-dimethyl, 2,5-dimethyl, 3,4-dichloro, 2,5-dichloro, 5-chloro-2-methyl, 2-chloro-5-methyl, 4-chloro-3-methyl, 3-chloro-4-methyl, 3-chloro-2-methyl, 4-chloro-2-methyl, 2-chloro-6-methyl and 2-chloro-4-methyl; and n is an integer from about 10 to about 100;

said amylose derivative coated on a porous inorganic carrier or a porous organic carrier;

(b) providing a flow of a solvent system through said column;

(c) adsorbing a mixture of tofisopam enantiomers onto the chiral separation medium;

(d) passing a first amount of the solvent system through the chromatography column sufficient to elute from said chiral separation medium substantially all of the (S)-enantiomer of tofisopam present in the mixture of tofisopam enantiomers, substantially free of the (+) conformer of (R)-tofisopam; and (e) passing a second amount of the solvent system through the chromatography column, sufficient to elute from the chiral separation medium the (+)-conformer of (R)-tofisopam substantially free of the (S)-enantiomer of tofisopam.

24. The method according to claim 23 wherein the chiral separation medium comprises an amylose derivative of formula I, and the solvent system comprises a mixture of acetonitrile and methanol.

25. The method according to claim 23 wherein the chiral separation medium comprises a (2S)-2-{(1S)[(3,5-dinitrophenyl)carbonylamino]-phenylmethyl}-3,3-dimethylbutanoate covalently bound to silica, and the solvent system comprises a mixture of heptane and ethanol.

* * * * *